United States Patent [19]

Suzuki

[11] Patent Number: 4,740,465

[45] Date of Patent: Apr. 26, 1988

[54] HEAT-RESISTANT SARCOSINE OXIDASE N AND PROCESS FOR PRODUCING THE SAME

[75] Inventor: Masaru Suzuki, Kashiwa, Japan

[73] Assignee: Noda Institute for Scientific Research, Japan

[21] Appl. No.: 809,864

[22] Filed: Dec. 17, 1985

[30] Foreign Application Priority Data

Jan. 11, 1985 [JP] Japan .................................. 60-1989

[51] Int. Cl.$^4$ .......................... C12N 9/06; C12R 1/07; C12Q 1/26
[52] U.S. Cl. .................................. 435/191; 435/832; 435/25
[58] Field of Search ................................ 435/191, 25

[56] References Cited

U.S. PATENT DOCUMENTS 4,216,292 8/1980 Ikuta .................................. 435/191

FOREIGN PATENT DOCUMENTS 56-92790 7/1981 Japan .................................. 435/191
61-162174 7/1986 Japan .

OTHER PUBLICATIONS

Suzuki, "Purification and Some Properties of Sarcosine Oxidase from *Corynebacterium* sp. U-96", J. Biochem., 89, 599–607, (1981).

*Primary Examiner*—Lionel M. Shapiro
*Attorney, Agent, or Firm*—Banner, Birch, McKie and Beckett

[57] ABSTRACT

When a microorganism belonging to the genus Bacillus and capable of producing heat-resistant sarcosine oxidase N is cultured in a medium, there can be obtained from the cultured medium, heat-resistant sarcosine oxidase N having the following physico-chemical properties:

(a) Action

Sarcosine oxidase N catalyses the following enzyme reaction wherein sarcosine is oxidatively decomposed to form glycine, formaldehyde and hydrogen peroxide.

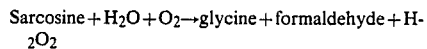

(b) Substrate specificity

Sarcosine oxidase N has a Km value (Michaelis constant) for sarcosine of 4.7 mM at 37° C. at pH 7.7 (phosphate buffer solution).

(c) Optimum pH and stable pH range

The optimum pH of sarcosine oxidase N is 6.7 to 10.0 when sarcosine is used as a substrate.

The stable pH range is 6.5 to 11.5.

(d) Optimum temperature range

45° to 60° C.

(e) Heat stability

Sarcosine oxidase N retains its enzymatic activity of 98% when treated at 55° C. for 10 minutes and of 75% even when treated at 60° C. for 10 minutes.

(f) Molecular weight

About 49,000 when measured by gel filtration method using Sephadex G-150.

(g) Flavin enzyme protein

Sarcosine oxidase N contains 1 mole of covalently bound flavin adenine dinucleotide (FAD) per mole of the enzyme.

6 Claims, 2 Drawing Sheets

HEAT-RESISTANT SARCOSINE OXIDASE N AND PROCESS FOR PRODUCING THE SAME

BACKGROUND OF THE INVENTION

1. Field of the Invention

This invention relates to novel, heat-resistant sarcosine oxidase N and a process for producing the same.

2. Description of the Prior Art

Sarcosine oxidase is an enzyme which catalyzes the following reaction.

$$\text{Sarcosine} + H_2O + O_2 \rightarrow \text{glycine} + \text{formaldehyde} + H_2O_2$$

Sarcosine oxidase is known and described in, for example, U.S. Pat. No. 4,216,292 and J. Biochem. 89, 599 (1981), JAPAN.

Meanwhile, in the field of clinical medicine, quantitative determination of creatinine or creatine present in serum and urine is currently conducted for examination of renal function disorder, muscular disorder, etc. For this determination, there is known a so-called Jaffé method wherein creatinine is reacted with alkaline picric acid and the resulting orange color is measured. This color-developing reaction is affected by various substances present in serum and urine and accordingly is a non-specific reaction. Consequently, the value obtained by the Jaffé method is low in reliability. Moreover, since a step for protein removal is necessary in many cases, the method is troublesome in procedure.

A method for enzymatically determining creatinine or creatine has recently been reported [Clinical Science Symposium No. 19, 196 (1979)]. This method uses sarcosine oxidase as shown below. In the following formulas, the enzymes used are given in parentheses.

$$\text{Creatinine} + H_2O \rightleftharpoons \text{creatine}$$

(Creatinine amidohydrolase)

$$\text{Creatine} + H_2O \rightarrow \text{sarcosine} + \text{urea}$$

(Creatine amidinohydrolase)

$$\text{Sarcosine} + H_2O + O_2 \rightarrow \text{glycine} + \text{formaldehyde} + H_2O_2$$

(Sarcosine oxidase)

However, since the amount of creatinine or creatine present in serum and urine is very small, there has been desired the development of a high sensitivity method for enzymatic determination of creatinine or creatine.

A coloring agent has recently been developed which develops a color at a high sensitivity when hydrogen peroxide ($H_2O_2$) is treated, under neutrality or slight acidity, with a peroxidase obtained from horseradish. This color is blue or green and is different from yellow or red originated from serum components; therefore, no blank measurement for serum is necessary, which is advantageous. However, the above color is unstable and disappears at pH 7.5 or above. Consequently, it is necessary to conduct the enzymatic reaction/color-developing reaction under neutrality or slight acidity to expect a stable color-developing reaction. Moreover, since the optimum pH of peroxidase is at or around 6.5 (slight acidic), the coupled enzymes are also required to have a satisfactory enzymatic action under slight acidity.

The enzymes used for determination of creatinine or creatine are required to be highly pure and free from other accompanying enzymes. Therefore, there is desired the development of enzymes of high relative activity and high purity which can be obtained from a mass purification step wherein other accompanying enzymes (e.g. catalase and uricase) are completely inactivated by a heat treatment.

Since the amount of creatinine or creatine contained in serum and urine is small, the amount of sarcosine formed from the enzymatic decomposition of creatinine or creatine is inevitably small. Therefore, there is strongly desired in the industry the development of an enzyme which can act on even such a small amount of sarcosine and has a small Km value (Michaelis constant).

These tasks have been achieved by the present invention.

In view of the above situation, the present inventors conducted an extensive study in order to provide a novel sarcosine oxidase suitable for high sensitivity enzymatic determination of creatinine or creatine which has a satisfactory enzymatic action even under slight acidity, is thermally stable and has a low Km value for sarcosine. As a result, it was found that by culturing a strain belonging to genus Bacillus, newly isolated from the soil, there can be obtained a novel sarcosine oxidase having a satisfactory enzymatic activity even under slight acidity, being heat-resistant and having a low Km value for sarcosine. This finding has led to the completion of the present invention.

SUMMARY OF THE INVENTION

The present invention provides heat-resistant sarcosine oxidase N having the following physico-chemical properties.

(a) Action

Sarcosine oxidase N catalyses the following enzyme reaction wherein sarcosine is oxidatively decomposed to form glycine, formaldehyde and hydrogen peroxide.

$$\text{Sarcosine} + H_2O + O_2 \rightarrow \text{glycine} + \text{formaldehyde} + H_2O_2$$

(b) Substrate specificity

Sarcosine oxidase N has a Km value (Michaelis constant) for sarcosine of 4.7 mM at 37° C. at pH 7.7. (phosphate buffer solution).

(c) Optimum pH and stable pH range

The optimum pH of sarcosine oxidase N is 6.7 to 10.0 when sarcosine is used as a substrate.

The stable pH range is 6.5 to 11.5.

(d) Optimum temperature range

45° to 60° C.

(e) Heat stability

Sarcosine oxidase N retains its enzymatic activity of 98% when treated at 55° C. for 10 minutes and of 75% even when treated at 60° C. for 10 minutes.

(f) Molecular weight

About 49,000 when measured by gel filtration method using Sephadex G-150.

(g) Flavin enzyme protein

Sarcosine oxidase N contains 1 mole of covalently bound flavin adenine dinucleotide (FAD) per mole of the enzyme.

The present invention further provides a process for producing heat-resistant sarcosine oxidase N, which comprises culturing in a medium a microorganism belonging to the genus Bacillus and capable of producing heat-resistant sarcosine oxidase N and then collecting the heat-resistant sarcosine oxidase N produced from the cultured medium thereof.

BRIEF DESCRIPTION OF THE DRAWINGS

In the accompanying drawings.

DETAILED DESCRIPTION OF THE INVENTION

Figure 1:
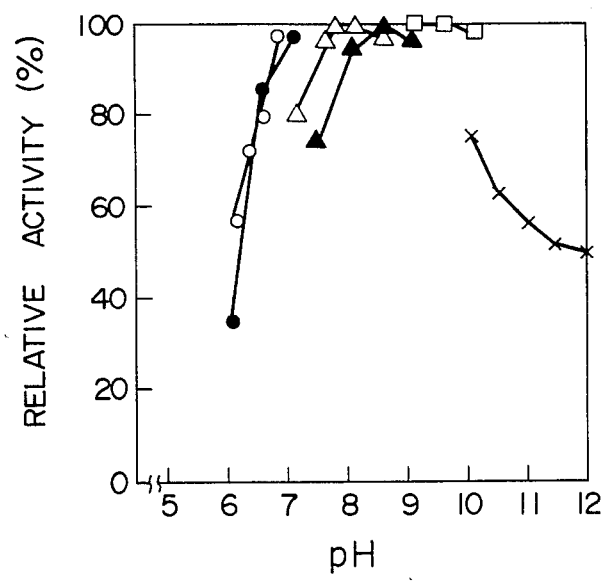
FIG. 1 shows the optimum pH of the present enzyme.

The physico-chemical properties of the present enzyme (heat-resistant sarcosine oxidase N) when purified will be described in detail below.

(1) Action

The present enzyme catalyses the following enzyme reaction wherein sarcosine is oxidatively decomposed to form glycine, formaldehyde and hydrogen peroxide.

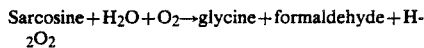

$$Sarcosine + H_2O + O_2 \rightarrow glycine + formaldehyde + H_2O_2$$

(2) Substrate specificity

The substrate specificity of the present enzyme was examined under the following reaction conditions.

To 0.5 ml of a 0.2 M substrate solution, 0.1 ml of a 0.3 M phosphate buffer solution of pH 7.7, 0.1 ml of a 0.2% 2,4-dichlorophenol sulfonate solution, 0.1 ml of a 4-aminoantipyrine (70 mg/dl) solution and 0.1 ml of a peroxidase (70 units/ml) solution was added 0.1 ml of a solution containing 17 units/ml (when necessary, diluted appropriately with a 0.3 M phosphate buffer solution of pH 7.7) of the present invention enzyme (heat-resistant sarcosine oxidase N). The resulting mixture was incubated at 37° C. for 10 minutes. The reaction was stopped by adding 2 ml of 0.5 N acetic acid. The absorbance of the reaction mixture at 510 nm was measured using, as a control, the same reaction mixture of 0 reaction time. The relative activity for a substrate was expressed as a percentage of the absorbance at 510 nm when the substrate was subjected to the above enzyme reaction over the absorbance at 510 nm when N-methylglycine (sarcosine) was subjected to the same enzyme reaction.

| Substrate | Relative activity (%) |
|---|---|
| N—methylglycine (sarcosine) | 100 |
| N—methyl-L-alanine | 31.3 |
| N—methyl-L-valine | 7.3 |
| N—methyl-L-isoleucine | 5.3 |
| N—methyl-L-serine | 0 |
| N—methyl-L-glutamic acid | 0 |
| N—methyl-L-lysine | 0 |
| Sarcosylglycine | 0 |
| Glycine | 0.09 |
| L-alanine | 0 |
| L-valine | 0 |
| L-isoleucine | 0 |
| L-threonine | 0 |
| L-serine | 0 |
| D-glutamic acid | 0 |
| D-aspartic acid | 0 |
| Tyramine | 0 |
| Histamine | 0 |
| N,N—dimethylglycine | 0 |
| Betaine | 0 |
| Choline | 0 |
| 1,3-Dimethylurea | 0 |
| 1-Methylguanidine | 0 |

The present enzyme has a Km value (Michaelis constant) for sarcosine of 4.7 mM at 37° C. at pH 7.7 (phosphate buffer solution).

(3) Optimum pH

The optimum pH of the present enzyme is 6.7 to 10.0 when sarcosine is used as a substrate, as shown in FIG. 1. In FIG. 1, ○—○ represents a PIPES buffer solution (pH 6.0 to 6.7); ●—● a 2,2-dimethyl glutarate buffer solution (pH 6.0 to 7.0); △—△ a phosphate buffer solution (pH 7.0 to 8.5); ▲—▲ a tris-HCl buffer solution (pH 7.5 to 9.0); □—□ a glycine-NaOH buffer solution (pH 9.0 to 10.0); and ×—× a glycing-NaCl-NaOH buffer solution (pH 10.0 to 12.0).

(4) Enzyme assay

First method: Sarcosine is oxidatively decomposed using the present enzyme and the resulting formaldehyde is determined by colorimetry.

To 0.3 ml of a 0.2 M sarcosine solution were added 0.1 ml of a 0.3 M phosphate buffer solution (pH 7.7) and 0.1 ml of a solution containing an appropriate concentration of the present enzyme. They were subjected to reaction at 37° C. for 10 minutes. The reaction was stopped by addition of 0.5 ml of a 1.0 N acetic acid solution. Thereto was added 3 ml of a color reagent (pH 6.5) containing 0.02% (V/V) of acetylacetone and 10% (W/V) of diammonium hydrogen phosphate. The resulting mixture was subjected to color development at 37° C. for 40 minutes. The absorbance of the resulting color at 410 nm was measured using a photoelectric photometer.

Using a calibration curve between formaldehyde amount and absorbancy, prepared in advance, there was obtained an amount of formaldehyde corresponding to the absorbance obtained above. From the amount, there was calculated an amount of the present enzyme necessary for production of formaldehyde of 1 μmole per minute at 37° C. This amount of the present enzyme was defined as 1 unit.

Second method: Sarcosine is oxidatively decomposed using the present enzyme and the resulting hydrogen peroxide ($H_2O_2$) is determined by colorimetry.

0.1 ml of a solution containing an appropriate concentration of the present enzyme was added to a mixture of 0.5 ml of a 0.2 M sarcosine solution, 0.1 ml of a 0.3 M phosphate buffer solution (pH 7.7), 0.1 ml of a 0.2% 2,4-dichlorophenol sulfonate solution, 0.1 ml of a 70 mg/100 ml 4-aminoantipyrine solution and 0.1 ml of a 70 units/ml peroxidase solution. This mixture was incubated at 37° C. for 10 minutes. The reaction was stopped by addition of 2 ml of a 0.5 N acetic acid solution. The absorbance of the resulting color at 510 nm was measured using a photoelectric photometer.

Using a calibration curve between hydrogen peroxide amount and absorbance, prepared in advance, there was obtained an amount of hydrogen peroxide corresponding to the absorbance obtained above. From the amount, there was calculated an amount of the present enzyme necessary for production of hydrogen peroxide of 1μ mole per minute at 37° C. This amount of the present enzyme was defined as 1 unit.

(5) Optimum temperature range

Figure 2:
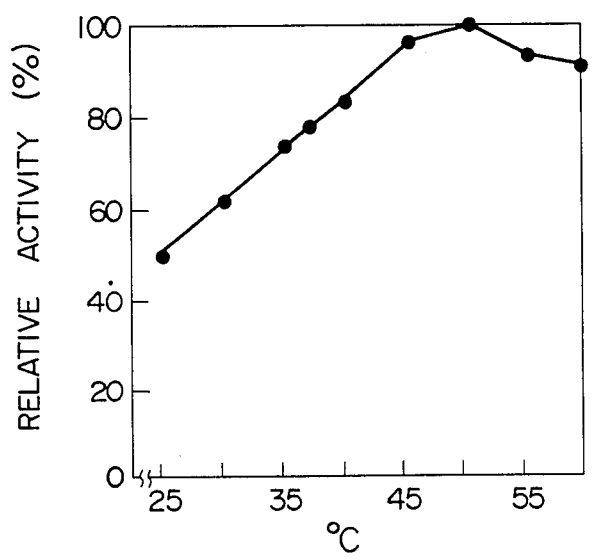
FIG. 2 shows the optimum temperature range of the present enzyme.

The optimum temperature range of the present enzyme is 45° to 60° C., as shown in FIG. 2.

Figure 3:
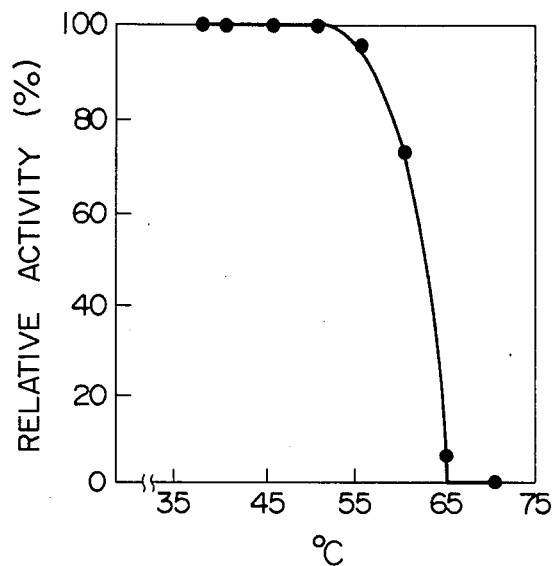
FIG. 3 shows the heat stability of the present enzyme.

(6) Heat stability 0.1 ml of a 0.3 M phosphate buffer solution (pH 7.7) containing 0.1 unit of the present enzyme purified was allowed to stand at various temperatures for 10 minutes to examine residual enzymatic activities after respective standings. The results are shown in FIG. 3. As seen in FIG. 3, the present enzyme purified had a residual activity of 75% even after incubating at 60° C. The activity of the present enzyme did not decrease at all after a treatment of 50° C. and 30 minutes. The enzyme retained its activity of 98% after a treatment of 55° C. and 10 minutes.

Figure 4:
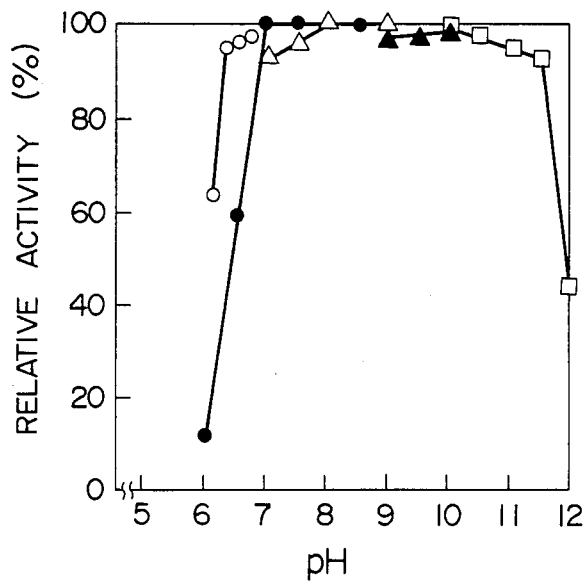
FIG. 4 shows the pH stability of the present enzyme.

(7) pH stability 0.5 ml of each buffer solution containing 0.19 unit of the present enzyme was allowed to stand at 5° C. for 48 hours to examine a residual enzymatic activity. The results are shown in FIG. 4. As seen in FIG. 4, the present enzyme was stable at a pH range of 6.5 to 11.5. In FIG. 4, O—O represents a PIPES buffer solution (pH 6.0 to 6.7); ●—● a phosphate buffer solution (pH 6.0 to 8.5); △—△ a tris-HCl buffer solution (pH 7.0 to 9.0); ▲—▲ a glycine-NaOH buffer solution (pH 9.0 to 10.0); □—□ and a glycine-NaCl-NaOH buffer solution (pH 10.0 to 12.0).

(8) Inhibition, activation and stabilization

The present enzyme is strongly inhibited by each 2 mM of $Cu^{2+}$, $Zn^{2+}$, $Ag^+$, $Hg^{2+}$, monoiodoacetic acid, potassium cyanide and N-ethylmaleimide.

There is no particular activator or stabilizor.

(9) Purification

The present enzyme can be purified according to a purification method which is described later.

(10) Molecular weight

The molecular weight of the present enzyme was measured by a column gel filtration method using Sephadex G-150 manufactured by Pharmacia Co. of Sweden, in accordance with the Andrews method [P. Andrews, Biochem. J., 96, 595 (1965)]. As a result, the present enzyme had a molecular weight of 49,000 in a 0.01 M phosphate buffer solution containing 0.1 M of sodium chloride.

(11) Isoelectric point

The present enzyme had an isoelectric point (pI) of 5.30 as measured by the disc focusing electrophoresis method.

(12) Disc electrophoresis

The present enzyme was subjected to disc electrophoresis [3 mA/gel, 5° C., 64 minutes (migration time of separation gel)]using a gel of pH 9.4 according to Davis [B. J. Davis, Ann. New York Acad. Sci., 121, 404 (1964)]and then was stained with Coomassie Brilliant Blue G-250. As a result, there was seen a single band at a distance of 3.9 cm from the original point toward the anode (Bromophenol Blue migrated by 4.0 cm) when the acrylamide content in the gel was 7.5%. When the acrylamide content was 15%, there was seen a single band at a distance of 1.3 cm from the original point toward the anode.

(13) Flavin enzyme

The present enzyme is yellow and 1 mole of the enzyme protein contains 1 mole of flavin adenine dinucleotide (FAD) covalently bound to said enzyme protein.

The present enzyme having the above physicochemical properties is compared with conventional sarcosine oxidases in Table 1.

TABLE 1

| | Present enzyme | Known enzyme[*1] | Known enzyme[*2] |
|---|---|---|---|
| Optimum pH | 6.7 to 10.0 | around 9 | 7.7 to 8.5 |
| Km value for sarcosine | $4.7 \times 10^{-3}$ M (37° C., pH 7.7) | — | $3.4 \times 10^{-3}$ M (37° C., pH 7.7) |
| Heat stability | Stable after standing at 50° C. for 30 minutes. Retains its activity of 75% after standing at 60° C. for 10 minutes. | Stable after standing at 40° C. for 10 minutes. Completely deactivated after standing at 60° C. for 10 minutes. | Stable after standing at 37° C. for 10 minutes. Completely deactivated after standing at 45° C. for 10 minutes. |
| Isoelectric point | 5.30 | 4.7 | 4.33 |
| Molecular weight | 49,000 | 40,000 | 174,000 |
| Flavin enzyme | 1 mole of FAD[*3] is covalently bound to 1 mole of the enzyme protein. | — | 1 mole of the enzyme protein contains 1 mole of covalently bound FAD and 1 mole of non-covalently bound FAD. |
| Substrate specificity | Has no action on betaine, dimethylglycine and lysine. | Acts on betaine (0.03%), dimethylglycine (0.01%) and lysine (0.07%). | Has no action on betaine, dimethylglycine and lysine. |

[*1]The sarcosine oxidase described in U.S. Pat. No. 4,216,292.
[*2]The sarcosine oxidase described in J. Biochem. 89, 599 (1981) JAPAN.
[*3]Abbreviation of flavin adenine dinucleotide.

As stated above, the present enzyme is different from any known sarcosine oxidases in enzyme chemistry and physico-chemical properties and, in particular, has very high heat stability compared with conventional sarcosine oxidases. Therefore, the present enzyme is not inactivated when used at high temperature and is advantageous. Further, in the purification of the present enzyme on a large scale, other accompanying enzymes (e.g. catalase which decomposes $H_2O_2$) can be inactivated completely, whereby the present enzyme can easily be obtained in a high purity.

In addition, the present enzyme has a satisfactory enzymatic activity even under slight acidity unlike conventional sarcosine oxidases. This is particularly advantageous when a high sensitivity coloring agent enabling determination of a small amount of creatinine or creatine is used. The reason is as follows. Said coloring agent having a maximum absorbance at a long wavelength side (600 to 750 nm) develops a color at a high sensitivity but is very unstable at pH 7.2 or above; meanwhile, the optimum pH of the peroxidase used in the coupled reactions for determination of creatinine or creatine is around 6.5; hence, it becomes necessary to conduct the enzyme reaction for determination of creatinine or creatine, at pH 6.5 to 7.2; therefore, in this regard, the present enzyme is far more suitable than any conventional counterparts.

Next, the process for producing heat-resistant sarcosine oxidase N according to the present invention will be described.

The microorganism used in the present invention is a strain belonging to the genus Bacillus and capable of producing novel sarcosine oxidase N. Specific examples of the microorganism includes Bacillus sp. NS-129. Its variant or mutant may also be used. Bacillus sp. NS-129 is a strain newly isolated from the soil by the present inventor and has the following taxonomic properties.

(a) Morphology

Microscopic observation when cultured at 30° C. for 1 to 3 days in a bouillon agar medium.

(1) Size of cells: Bacillus of $1.3-1.9 \times 3.8-6.4\mu$.
(2) Polymorphism of cells: None
(3) Motility: Peritricic locomotion.
(4) Spore: Forms endospores in 2 to 3 days at the center or near the edge of cell. The shape of the spores is elliptical and its size is $1.5 \times 2.3\mu$. Cells are swollen by the spores.
(5) Gram's stain: Positive.
(6) Acid-fast stain: Negative.

(b) Growth in various media (1) Bouillon agar plate culture- Light grayish brown colonies are formed after 30° C. $\times$ 24 hours. These colonies have a smooth surface and a dim luster and is opaque. No pigment formation.
(2) Bouillon agar slant culture: Good growth. Same as in (1).
(3) Bouillon liquid culture: Growth is bad in stationary culture and grown bacterial cells precipitate.
(4) Bouillon gelatin stab culture: No liquefaction occurs even when cultured at 25° C. or 30° C. The bacterium grows also in shaking culture but no liquefaction is seen.
(5) Litmus milk: No change.

(c) Physiological properties (1) Nitrate reduction: Positive.
(2) Denitrification reaction: Negative.
(3) MP test: Negative.
(4) VP test: Negative.
(5) Formation of indole: Negative.
(6) Formation of hydrogen sulfide: Positive.
(7) Hydrolysis of starch: Negative.
(8) Hydrolysis of casein: Negative.
(9) Decomposition of uric acid (production of uricase): Negative.
(10) Decomposition of tyrosine: Negative.
(11) Hydrolysis of cellulose: Negative.
(12) Utilization of citric acid: Negative in Simons medium and positive in Christensen medium.
(13) Utilization of inorganic nitrogen: Utilizes ammonia but weak. Hardly utilizes nitrates.
(14) Urease: Negative.
(15) Oxidase: Positive.
(16) Catalase: Positive.
(17) Formation of pigment: Negative.
(18) Salt resistance: Grows up to 5% (NaCl).
(19) Behavior for oxygen: Aerobic.
(20) Ranges of growth: The pH range for growth is 6.0 to 9.0. The temperature range for growth is 25° to 45° C.
(21) Extinction temperature: Does not get extinct in a treatment of 80° C. $\times$ 30 minutes. Complete extinction in a treatment of 85° C. $\times$ 30 minutes.
(22) O-F test: No reaction. No change in an agar medium using glycerol or glucose. In an aerobic shaking culture, the bacterium grew well in a peptoneyeast extract medium but there was no formation of acid.
(23) Formation of acids and gases from saccharides: Acid formation was examined in stationary culture as well as in shaking culture. Gas formation was examined in stationary culture. As a result, neither acid nor gas was formed from the following saccharide used. Inositol, D-galactose, D-mannose, D-ribose, trehalose, L-arabinose, D-xylose, erythritol, L-rhamnose, mannitol, sucrose, maltose, fructose, lactose, D-arabinose, L-sorbose, L-rhamnose, dextrin, sorbitol, D-(+)raffinose, salicin, inulin, D(+)-melibiose, glycerin, glucose, cellobiose, melezitose, xylitol.

(d) Other properties

Grows well in a medium containing vitaminefree casamino acid, potassium phosphate and $MgSO_4 \cdot 7H_2O$.

When the taxonomic properties of the present strain capable of producing heat-resistant sarcosine oxidase N is compared with the classification of Bergey's Manual of Determinative Bacteriology, 8th Edition (1974), it is considered that the present strain belongs to the genus Bacillus because it is a bacillus which is positive in Gram's stain and forms aerobic endospores and further that the present strain is either of *Bacillus firmus, Bacillus brevis, Bacillus fastidiosus, Bacillus freudenreichii, Bacillus badius*, etc. because the spores formed by the present strain are elliptical to oval and are located around the center of bacterial cell and the present strain forms neither acid nor gas from glucose, forms no acetoin, is very aerobic and does not grow at 3° C. However, since *Bacillus firmus* oxidatively forms acids from glucose and demands biotin, *Bacillus fastidiosus* vigorously decomposes uric acid to become alkaline and does not reduce nitric acid, *Bacillus freudenreichii* utilizes urea to become alkaline and *Bacillus badius* forms root-shaped or woolly colonies in growth, the present strain is different from these Bacilli. The present strain is most similar to *Bacillus brevis* in properties but is also different from it in hydrolysis of tyrosine and growth in 5% NaCl. Hence, the present strain was designated as Bacillus sp. NS-129. Effective Dec. 3, 1984, Bacillus sp. NS-129 was deposited in Fermentation Research Institute, Agency of Industrial Science and Technology, Japan in compliance with the Budapest Treaty on the International Recognition of the Deposit of Microorganisms for the purposes of patent procedure and was given an accession No. FERM BP-671.

The culture medium used in the present invention can be any synthetic or natural medium as long as it contains an appropriate combination of a carbon source, a nitrogen source, inorganic salts and other nutrients. As the carbon source, there can be used, for example, creatinine, creatine, sarcosine, citric acid and fatty acids. As the nitrogen source, there can preferably be used, for example, protein type substances and their digests such as peptone, casein digest and soybean powder as well as nitrogen-containing organic substances such as yeast extract. As the inorganic salts, there can be used, for example, salts of sodium, potassium, manganese, magnesium, calcium, iron, cobalt and the like.

In the present invention, heat-resistant sarcosine oxidase N can be obtained in the highest yield when the present strain is cultured in a medium containing creatinine, creatine or sarcosine. As a preferable example of such a culture medium, there can be mentioned, for example, a medium of pH 6.5 containing 0.8% of sarcosine, 0.8% of yeast extract, 2% of a polypeptone, 0.05% of potassium biphosphate, 0.05% of potassium diphosphate, 0.01% of magnesium sulfate and 0.005% of iron sulfate.

Culture of the present strain is conducted ordinarily at 25° to 40° C., preferably at or around 30° C. The initial pH of the culture medium is ordinarily 6 to 8, preferably around 6.5. By conducting a shaking culture or a submerged stirring culture for 16 to 24 hours under such conditions, heat-resistant sarcosine oxidase N can be formed and accumulated effectively in the cultured medium.

At times, long culture time causes bacteriolysis of the present strain and resulting production of the present enzyme outside their cells. However, the present enzyme is ordinarily present within the cells. Therefore, the cultured medium is subjected to centrifugation, filtration or the like to collect bacterial cells. The cells collected are destroyed in a proper amount of a buffer solution according to an ultrasonic method, a method using a bacteriolytic enzyme, a chemical self digestion method or any other proper method, whereby the present enzyme is solubilized and isolated in the solution. From the enzyme-containing solution thus obtained are removed nucleic acid and cell walls according to an ordinary method. Insolubles are then removed by filtration or centrifugation to obtain heat-resistant sarcosine oxidase N.

The present enzyme obtained above is subjected, as necessary, to ordinary isolation and purification of enzyme. For example, the above enzyme can be subjected to (1) column chromatography using a DEAEcellulose, (2) fractionation using ammonium sulfate, (3) column chromatography using QAE-Sephadex, (4) hydrophobic chromatography using TSK-Gel butyl-Toyo Pearl 650C manufactured by TOYO SODA MFG. CO., LTD., (5) gel filtration using Sephadex, or (6) an appropriate combination thereof, whereby the present enzyme can be obtained in a purified form. An example of purification of the present enzyme is described below.

The bacterial cells collected from the cultured medium are suspended in a 0.01 M phosphate buffer solution of pH 8.0. Thereto is added a lysozyme at a proportion of 50 mg/l and bacteriolysis is allowed to take place at 37° C. for 30 minutes. Then, thereto is added a nucleic acid-removing agent such as manganese sulfate, a polyethylimine, protamine sulfate, streptomycin or the like. The resulting precipitate is removed by cellulose filtration. The resulting enzyme solution is treated at 50° C. for 1 to 2 hours, after which the solution is again subjected to cellulose filtration. The filtrate is allowed to be adsorbed by QAE-Sephadex A-50 packed in a column and previously buffered with a 0.01 M phosphate buffer solution of pH 8.0, is washed with a 0.01 M phosphate buffer solution of pH 8.0 containing 0.1 M sodium chloride, and then is subjected to concentration gradient elution using 0.1 to 0.6 M NaCl solutions. The active fractions eluted are combined. Therein is dissolved ammonium sulfate at a proportion of 20 g/100 ml. The resulting solution is allowed to be adsorbed by TSK-GEL bytulToyo Pearl 650C (manufactured by TOYO SODA MFG. CO., LTD.) packed in a column and previously buffered with a 0.01 M phosphate buffer solution of pH 8.0 containing 20% ammonium sulfate, is washed with the same buffer solution, and then is subjected to elution using a 0.01 M phosphate buffer solution of pH 8.0 containing 10% ammonium sulfate, whereby a yellow enzyme is eluted. This active fraction is subjected to column chromatography using Sephadex G-150 previously buffered with a 0.01 M phosphate buffer solution of pH 8.0 containing 0.1 M NaCl, to obtain a fraction containing the present enzyme. The fraction is concentrated and freeze-dried to obtain a purified enzyme powder of the present enzyme.

The present invention provides heat-resistant sarcosine oxidase N which is a very useful diagnostic enzyme employed in examination of renal function disorder, muscular disorder, etc. as well as a process for producing said enzyme efficiently. Accordingly, the present invention has an important significance in industry.

An example of the present invention will be described below. However, the present invention is in no way restricted to the example.

EXAMPLE

Bacillus sp. NS-129 (FERM BP-671) was inoculated into 100 ml of a bouillon medium placed in a 500-ml Erlenmeyer flask, and culture was conducted at 30° C. for 16 hours. The seed cultured medium obtained was inoculated into 200 ml of an enzyme-producing medium of pH 6.5 containing 0.8% of sarcosine, 2% of a polypeptone, 0.8% of yeast extract, 0.05% of potassium biphosphate, 0.05% of dipotassium phosphate, 0.01% of magnesium sulfate and 0.005% of iron sulfate, placed in a 30-l jar fermenter. Culture was conducted at 30° C. for 18 hours under conditions of air flow of 20 l/min and stirring of 350 rpm. The resulting cultured medium was subjected to centrifugation to collect baceterial cells.

To part (110 g) of these bacetrial cells was added 1.5 l of a 0.01 M phosphate buffer solution (pH 8.0) and the cells were thoroughly dispersed in the solution. Thereto was added 100 mg of lysozyme obtained from egg white, and bacteriolysis was allowed to take place at 37° C. for 1 hour, followed by heating at 50° C. for 2 hours to denature other accompanying protein. Then, thereto was added a saturated solution (pH 7.5) of protamine sulfate until no precipitate was formed. Successively 5 g of a cellulose powder was added and, after thorough stirring, the mixture was filtered through a filter paper. The resulting filtrate was charged on a column of QAE-Sephadex A-50 (manufactured by Pharmacia Co., 3 cm$\omega$×40 cm), previously buffered with a 0.01 M phosphate buffer solution (pH 8.0) containing 0.05 M NaCl. Thorough washing was conducted using a 0.01 M phosphate buffer solution (pH 8.0) containing 0.1 M NaCl. Thereafter, the enzyme was eluted with a linear gradient of NaCl from 0.1 to 0.5 M. In active fractions of the eluate was dissolved ammonium sulfate at a proportion of 20 g/100 ml. This solution was allowed to be adsorbed by TSK-GEL butyl-Toyo Pearl 650C packed in a column (3 cm$\omega$×10 cm) and previously buffered with a 0.01 M phosphate buffer solution (pH 8.0) containing 20% ammonium sulfate, was washed with the same, ammonium sulfate-containing buffer solution, and was subjected to elution using a 0.01 M phosphate buffer solution containing 10% ammonium sulfate. The active ingredient fraction obtained was concentrated using an ultrafiltration apparatus (fractionation membrane 10,000) manufactured by Amicon Co., U.S.A. The concentrate was subjected to gel filtration using Sephadex G-150 packed in a column (1.2 cmω×100 cm) and previously buffered with a 0.01 M phosphate buffer solution (pH 8.0) containing 0.1 M NaCl. The active fraction obtained was concentrated to about 3 ml using an ultrafiltration apparatus and then freeze-dried, whereby 90.9 mg of a purified yellow enzyme powder was obtained. It had a relative activity of 30.1 units/mg and the recovery ratio was 17.1%.

What is claimed is:

1. Heat-resistant sarcosine oxidase N obtained by culturing Bacillus sp. NS-129 (FERM BP-671) and having the following physico-chemical properties:

(a) Action

Sarcosine oxidase N catalyzes the following enzyme reaction wherein sarcosine is oxidatively decomposed to form glycine, formaldehyde and hydrogen peroxide;

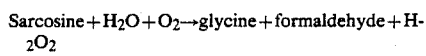

$$Sarcosine + H_2O + O_2 \rightarrow glycine + formaldehyde + H_2O_2$$

(b) Substrate specificity

Sarcosine oxidase N has a Km value (Michaelis constant) for sarcosine of 4.7 mM at 37° C. at pH 7.7 (phosphate buffer solution);

(c) Optimum pH and stable pH range

The optimum pH of sarcosine oxidase N is 6.7 to 10.0 when sarcosine is used as a substrate.

The stable pH range is 6.5 to 11.5;

(d) Optimum temperature range

45° to 60° C.

(e) Heat stability

Sarcosine oxidase N retains its enzymatic activity of 98% when treated at 55° C. for 10 minutes and of 75% even when treated at 60° C. for 10 minutes;

(f) Molecular weight

About 49,000 when measured in accordance with a column gel filtration method using Sephadex G-150;

(g) Flavin enzyme protein

Sarcosine oxidase N contains 1 mole of covalently bound flavin adenine dinucleotide (FAD) per mole of the enzyme.

2. A process for producing heat-resistant sarcosine oxidase N, which comprises culturing in a medium a microorganism Bacillus sp. NS-129 (FERM BP-671) capable of producing heat-resistant sarcosine oxidase N and then collecting the heat-resistant sarcosine oxidase N produced from the cultured medium thereof.

3. A process according to claim 2, wherein the medium contains a carbon source, a nitrogen source and an inorganic substance source.

4. A process according to claim 3, wherein the medium contains creatinine, creatine or sarcosine.

5. A process according to claim 2, wherein the culturing is conducted at 25° C. to 40° C. at pH 6 to 8.

6. A process according to claim 5, wherein the culturing is conducted for 16 to 24 hours in accordance with shaking culture or submerged stirring culture.

* * * * *